US012642482B2

(12) United States Patent
Kennedy

(10) Patent No.: US 12,642,482 B2
(45) Date of Patent: Jun. 2, 2026

(54) SYSTEMS AND METHODS FOR IMAGE MONITORING

(71) Applicant: ResMed Inc., San Diego, CA (US)

(72) Inventor: Colin Bradley Kennedy, San Diego, CA (US)

(73) Assignee: ResMed Inc., San Diego, CA (US)

( * ) Notice: Subject to any disclaimer, the term of this patent is extended or adjusted under 35 U.S.C. 154(b) by 0 days.

(21) Appl. No.: 18/816,783

(22) Filed: Aug. 27, 2024

(65) Prior Publication Data

US 2024/0415447 A1 Dec. 19, 2024

Related U.S. Application Data

(63) Continuation of application No. 17/623,185, filed as application No. PCT/US2020/039988 on Jun. 26, 2020, now Pat. No. 12,102,444.

(60) Provisional application No. 62/868,055, filed on Jun. 28, 2019.

(51) Int. Cl.
*A61B 5/00* (2006.01)
*G06T 7/00* (2017.01)

(52) U.S. Cl.
CPC ............ *A61B 5/445* (2013.01); *A61B 5/0077* (2013.01); *A61B 5/7275* (2013.01); *A61B 5/746* (2013.01); *G06T 7/0012* (2013.01); *A61B 2505/07* (2013.01); *G06T 2207/30088* (2013.01)

(58) Field of Classification Search
CPC ....... A61B 5/445; A61B 5/0077; A61B 5/746; A61B 2505/07; G06T 7/0012; G06T 2207/30088
See application file for complete search history.

(56) References Cited

U.S. PATENT DOCUMENTS

| | | | |
|---|---|---|---|
| 2017/0061621 A1 | 3/2017 | Wortman | |
| 2017/0236281 A1 | 8/2017 | Dacosta | |
| 2020/0193597 A1* | 6/2020 | Fan | H04N 25/135 |

FOREIGN PATENT DOCUMENTS

| | | | |
|---|---|---|---|
| EP | 3499510 A1 * | 6/2019 | G16H 40/63 |

OTHER PUBLICATIONS

Chakraborty et al.; "Telemedicine Supported Chronic Wound Tissue Prediction Using Classification Approaches"; J Med Syst, Jan. 4, 2016; pp. 1-12; vol. 40: 68; Springer Science & Business Media, LLC, New York US. (Year: 2016).*
International Search Report in International Patent Application No. PCT/US2020/039988 mailed Oct. 14, 2020 (4 pp.).
Written Opinion in International Patent Application No. PCT/US2020/039988 mailed Oct. 14, 2020 (7 pp.).
Dalya V. et al., "Design of Smartphone-based Wound Assessment System", International Journal of Computer Applications (0975-8887); Aug. 2016; pp. 12-15; vol. 147, No. 1.

(Continued)

*Primary Examiner* — Chao Sheng
(74) *Attorney, Agent, or Firm* — Nixon Peabody, LLP

(57) ABSTRACT

Accordingly, systems and methods have been developed to monitor, diagnose, and predict the course of a wound to aid in determining whether a wound is properly healing. This includes systems and methods that may be performed by the patient in the home in some cases, and some that utilized sensors available on mobile devices. Thus, patients may be able to manage wounds at home without the intervention of caregivers and reduce the costs of admission to hospitals.

20 Claims, 13 Drawing Sheets

(56)                    References Cited

OTHER PUBLICATIONS

Chen H. et al., "Wound Healing Monitoring by Video Sequence Using Integral Optical Flow", Journal of Applied Spectroscopy, Jul. 2019, pp. 435-442; vol. 86, No. 3, (Russian Original vol. 86, No. 3, May-Jun. 2019); 2019 Springer Science & Business Media, LLC.

Wang L. et al., "Wound Image Analysis System for Diabetics", Advances in Resist Technology and Processing XVI, Mar. 13, 2013; pp. 866924-1 to 866924-14; vol. 8669; US.

Chakraborty C. et al., "Telemedicine Supported Chronic Wound Tissue Prediction Using Classification Approaches", J Med Syst, Jan. 4, 2016; pp. 1-12; vol. 40: 68; Springer Science & Business Media, LLC, New York US.

Treuillet S. et al., "Three-Dimensional Assessment of Skin Wounds Using a Standard Digital Camera", IEEE Transactions on Medical Imaging, May 2009; pp. 752-762; vol. 28, No. 5; IEEE, US.

Yang, S. et al., "Sequential Change of Wound Calculated by Image Analysis Using a Color Patch Method during a Secondary Intention Healing"; PLOS | One, Sep. 20, 2016; pp. 1-15, DOI:10.1371/journal.pone.0163092.

Ozturk C. et al, "Measurement of wound healing by image analysis," Biomedical Science Instrumentation; Technical Papers Composing the Proceedings of the 32nd Annual Rocky Mountain Biomedical Symposium and 32nd International ISA Biomedical Sciences Instrumentation Symposium, Apr. 7-9, 1995; pp. 189-193, vol. 31, Instrument Society of America 1995.

West, John B., "Respiratory Physiology", 9th edition published 2012, Lippincott Williams & Wilkins.

\* cited by examiner

Nasal cavity

Oral cavity

Larynx

Vocal folds

Oesophagus

Trachea

Bronchus

Lung

Heart

Diaphragm

Alveolar sacs

SYSTEMS AND METHODS FOR IMAGE MONITORING

CROSS-REFERENCE TO RELATED APPLICATIONS

This application is a continuation of U.S. patent application Ser. No. 17/623,185, filed on Dec. 27, 2021, now allowed, which is a 371 National Phase Entry of International Patent Application No. PCT/US2020/039988, filed Jun. 26, 2020, which claims priority to and the benefit of U.S. Provisional patent application No. 62/868,055, filed Jun. 28, 2019, each of which is hereby incorporated by reference herein in its entirety.

1 BACKGROUND OF THE TECHNOLOGY 1.1 Field of the Technology
1.2 Description of the Related Art
1.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

1.2.2 Therapies

Various therapies, such as Continuous Positive Airway Pressure (CPAP) therapy, Non-invasive ventilation (NIV) and Invasive ventilation (IV) have been used to treat one or more of the above respiratory disorders.

1.2.3 Treatment Systems

These respiratory therapies may be provided by a therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

1.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include CPAP devices and ventilators. Examples of RPT devices include a CPAP device and a ventilator.

1.2.3.3 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

1.2.3.4 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

1.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

1.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculography (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

1.2.5 Wound Healing

Wound healing is heavily impacted by sleep and may even be more important than nutrition. At least one 2018 study showed that sleep had a greater impact than nutrition on wound healing times. Smith et al., "Impact of sleep restriction on local immune response and skin barrier restoration with and without 'multi-nutrition' nutrition intervention," App. Phys., Vol. 124, January 2018, the content of which is incorporated by reference herein in its entirety.

2 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, case of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of wounds.

An aspect of certain forms of the present technology is to provide methods and/or apparatus that improve the compliance of patients with respiratory therapy.

One form of the present technology comprises image processing techniques that identifies a wound healing trajectory.

Another aspect of one form of the present technology is the ability to alert caregivers if a wound is not healing within a normal range time.

Another aspect of one form of the present technology is the use of cameras and infrared sensors to sense color and surface temperature changes of wounds to determine their trajectory.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

3.2 Respiratory System and Facial Anatomy

FIG. 2A shows an overview of a human respiratory system including the nasal and oral cavities, the larynx, vocal folds, oesophagus, trachea, bronchus, lung, alveolar sacs, heart and diaphragm.

3.3 Patient Interface

FIG. 3A shows a patient interface in the form of a nasal mask in accordance with one form of the present technology.

3.4 RPT Device

FIG. 4A shows an RPT device in accordance with one form of the present technology.

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

3.5 Humidifier

3.6 Breathing Waveforms

Figure 6A:
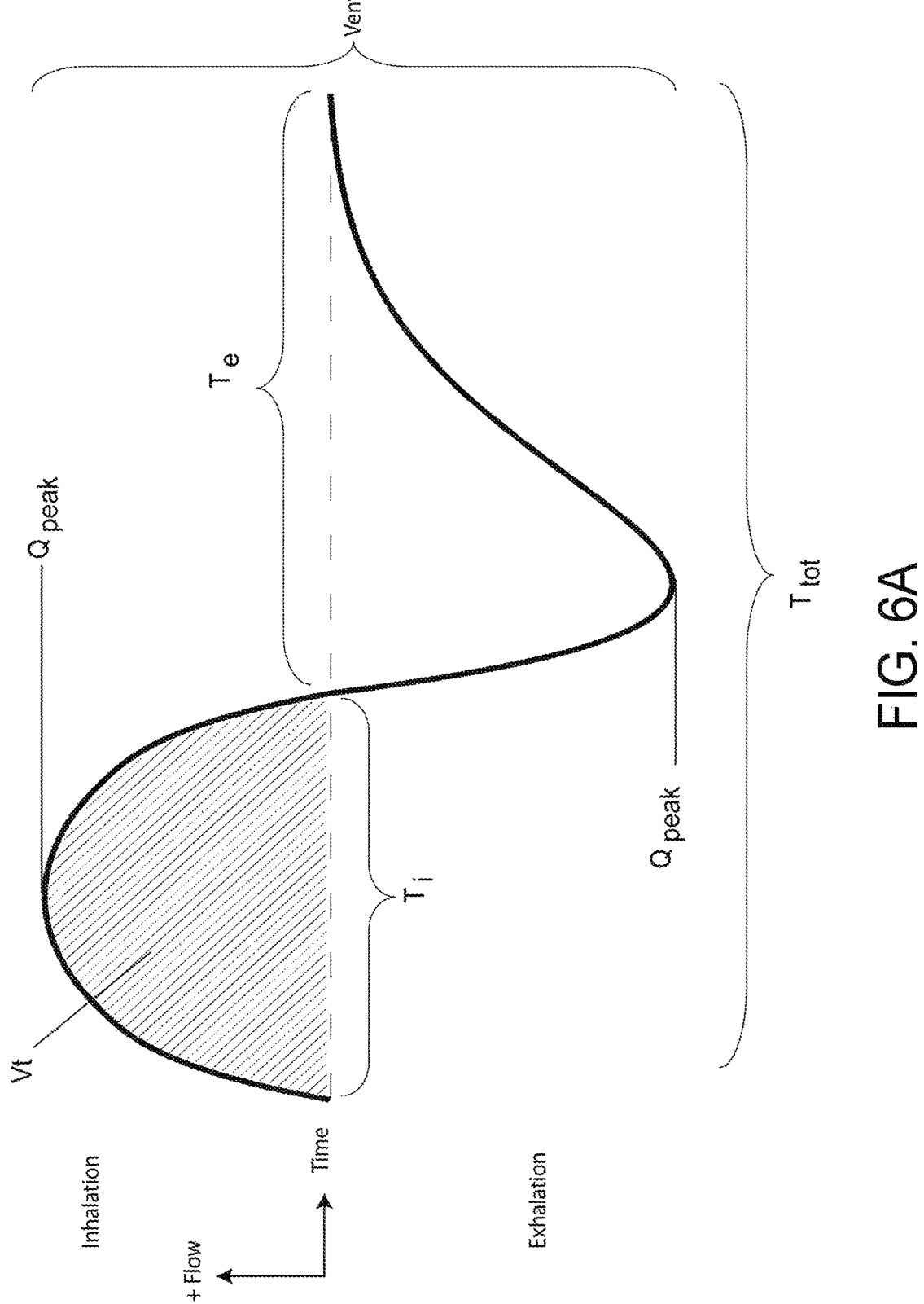

FIG. 6A shows a model typical breath waveform of a person while sleeping.

3.7 Screening, Diagnosis and Monitoring Systems

Figure 7:
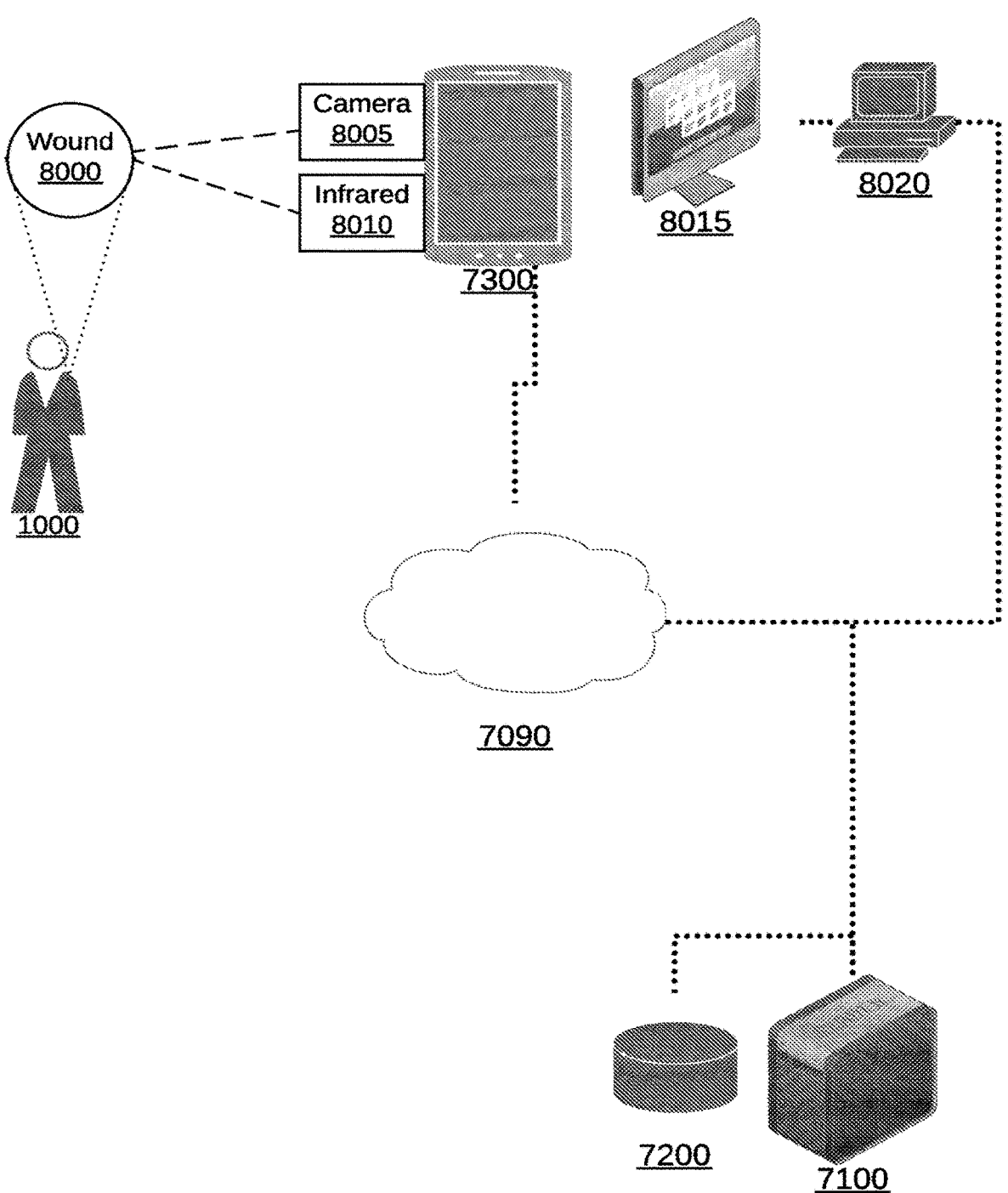

FIG. 7 shows an overview of an example system for monitoring a wound.

Figure 8:
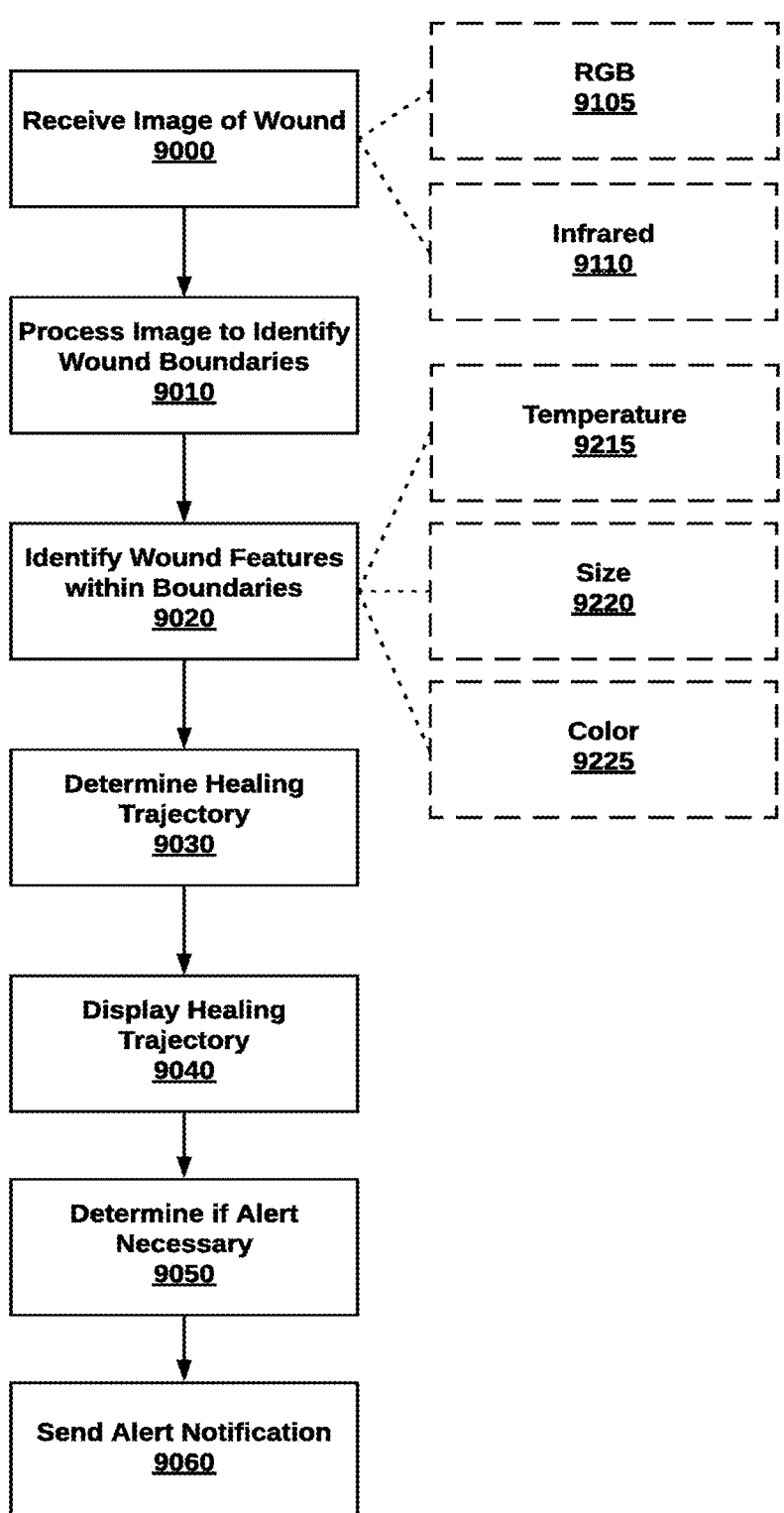

FIG. 8 shows a flow chart of an example process for monitoring a wound.

Figure 9:
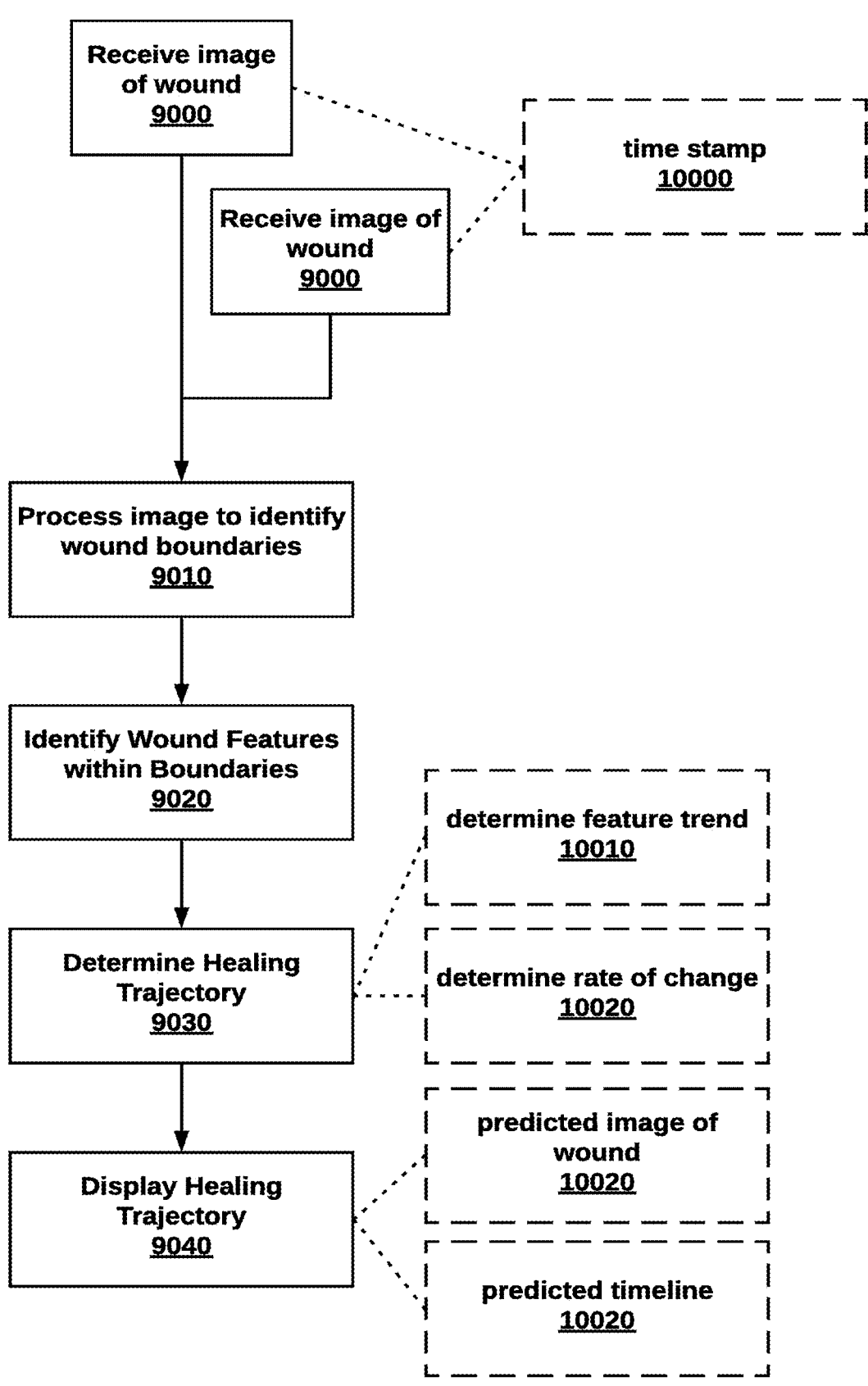

FIG. 9 shows a flow chart of an example process for monitoring a wound.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000 or 3800.

4.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

An unsealed patient interface 3800, in the form of a nasal cannula, includes nasal prongs 3810*a*, 3810*b* which can deliver air to respective nares of the patient 1000. Such nasal prongs do not generally form a seal with the inner or outer skin surface of the nares. The air to the nasal prongs may be delivered by one or more air supply lumens 3820*a*, 3820*b* that are coupled with the nasal cannula 3800. The lumens 3820*a*, 3820*b* lead from the nasal cannula 3800 lead to an RT device that generates the flow of air at high flow rates. The "vent" at the unsealed patient interface 3800, through which excess airflow escapes to ambient, is the passage between the end of the prongs 3810*a* and 3810*b* of the cannula 3800 via the patient's nares to atmosphere.

4.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10$cmH_2O$, or at least 20 $cmH_2O$.

4.5 Air Circuit

An air circuit 4170 in accordance with an aspect of the present technology is a conduit or a tube constructed and arranged to allow, in use, a flow of air to travel between two components such as RPT device 4000 and the patient interface 3000 or 3800.

4.5.1 Humidifier Overview

Figure 1A:
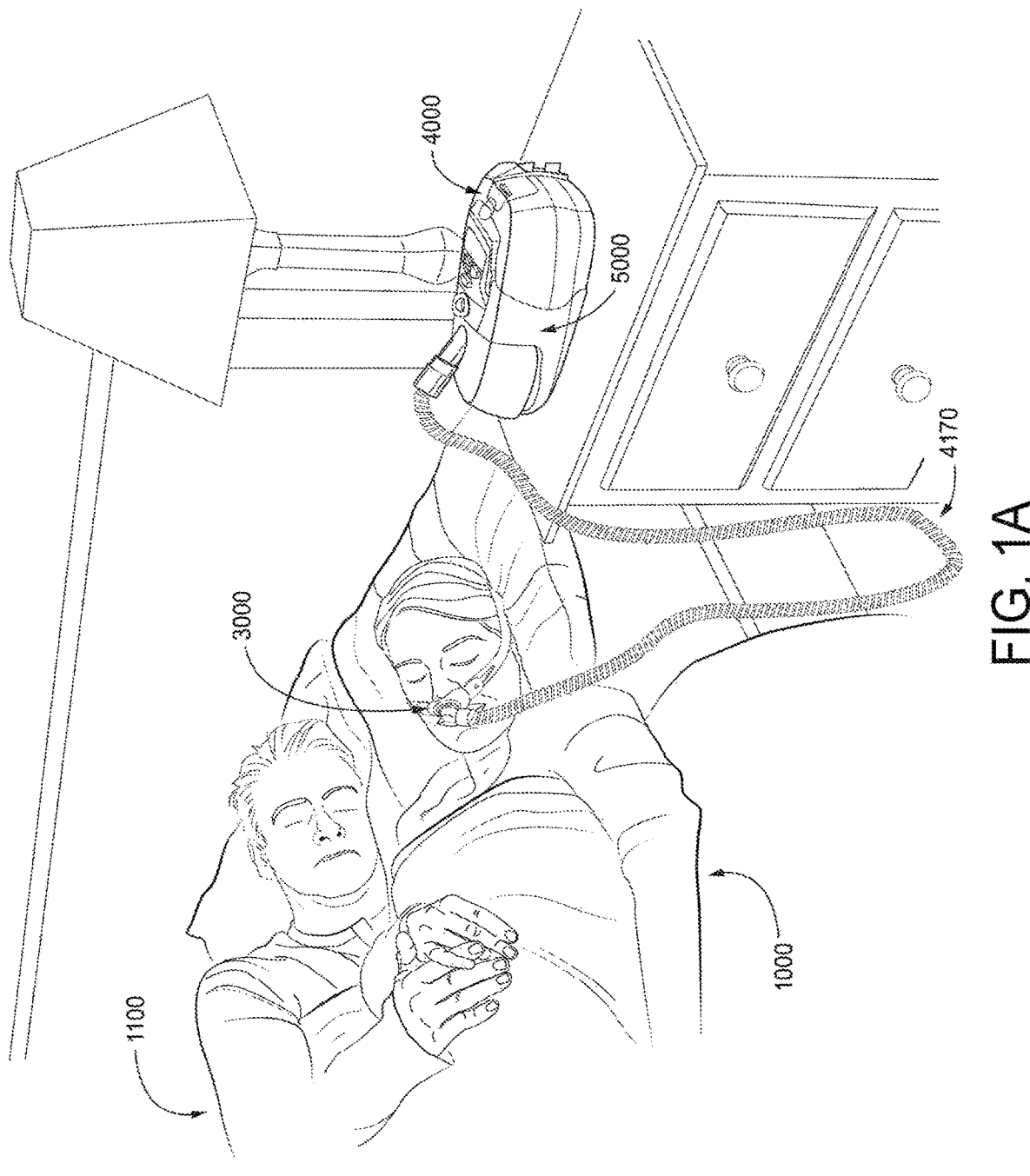
Figure 1B:
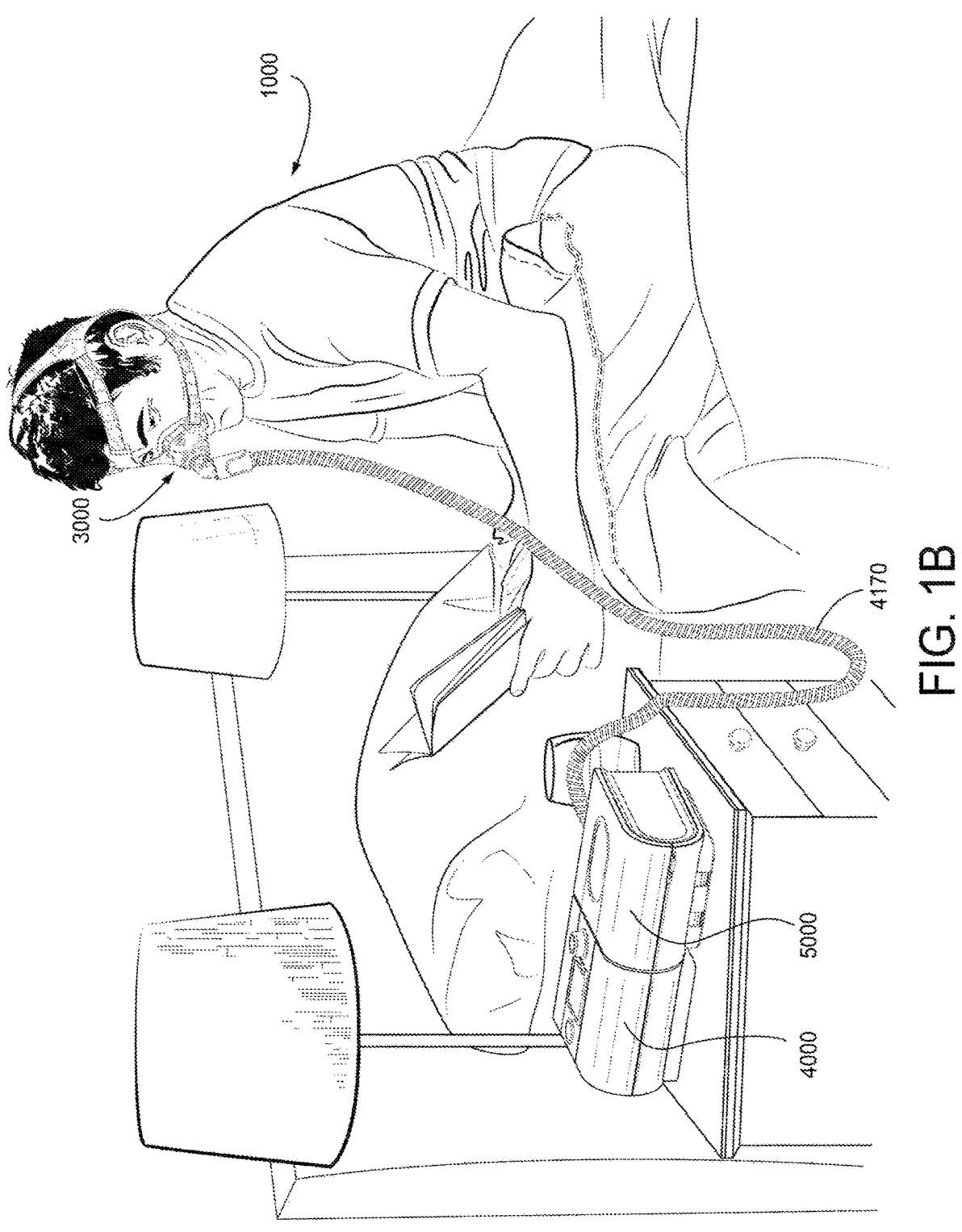
Figure 1C:
Figure 2A:
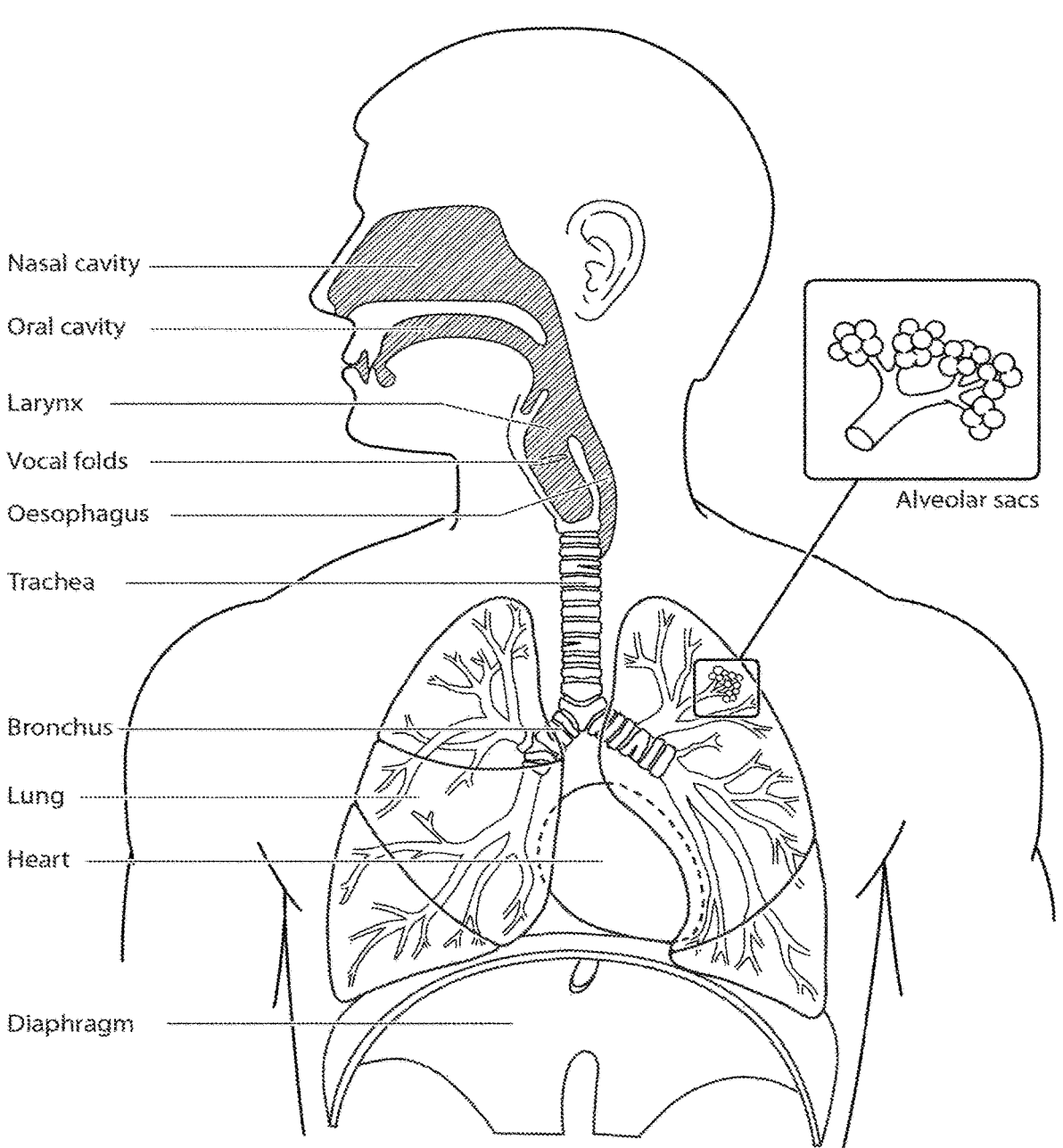
Figure 3A:
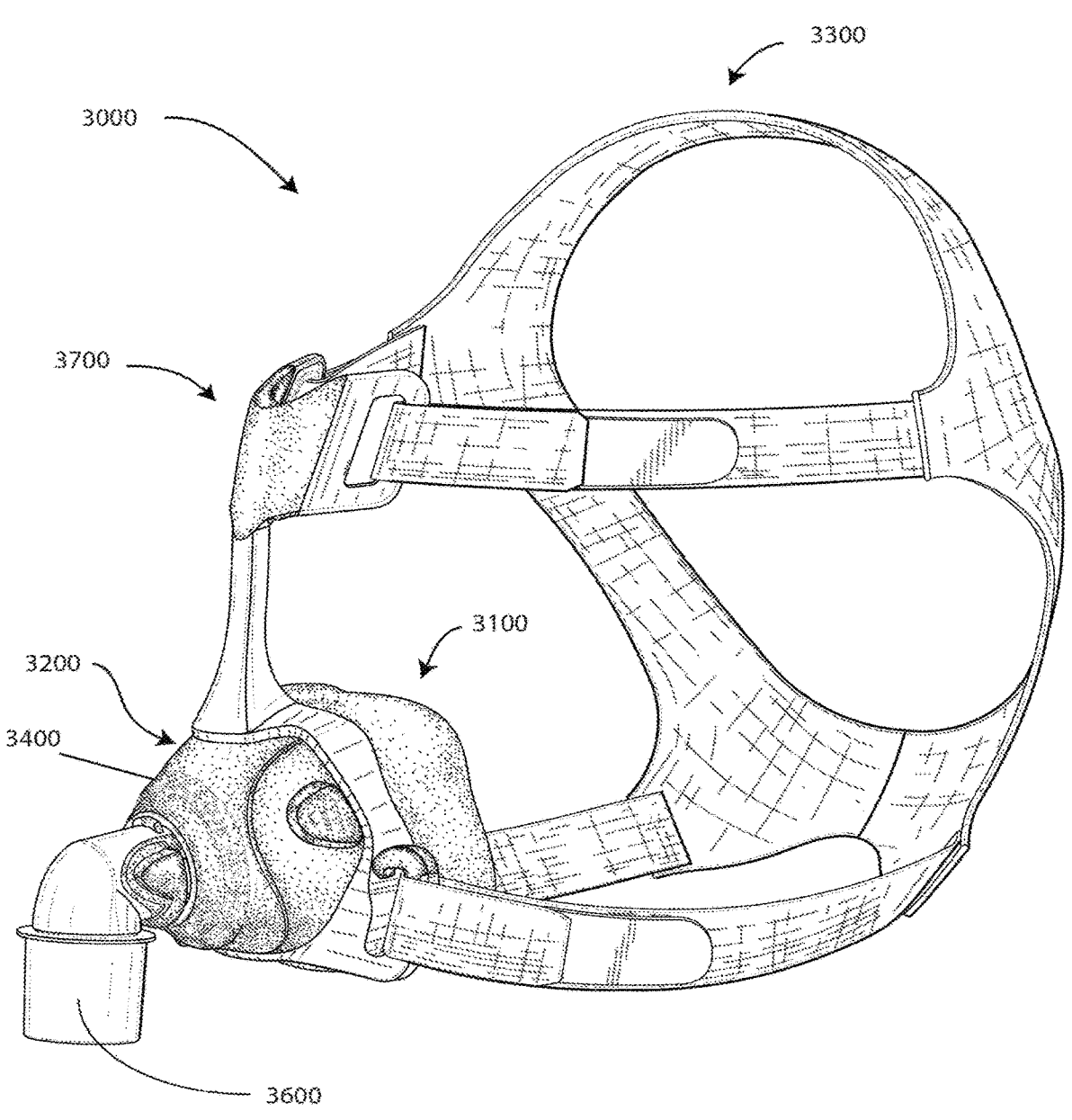
Figure 4A:
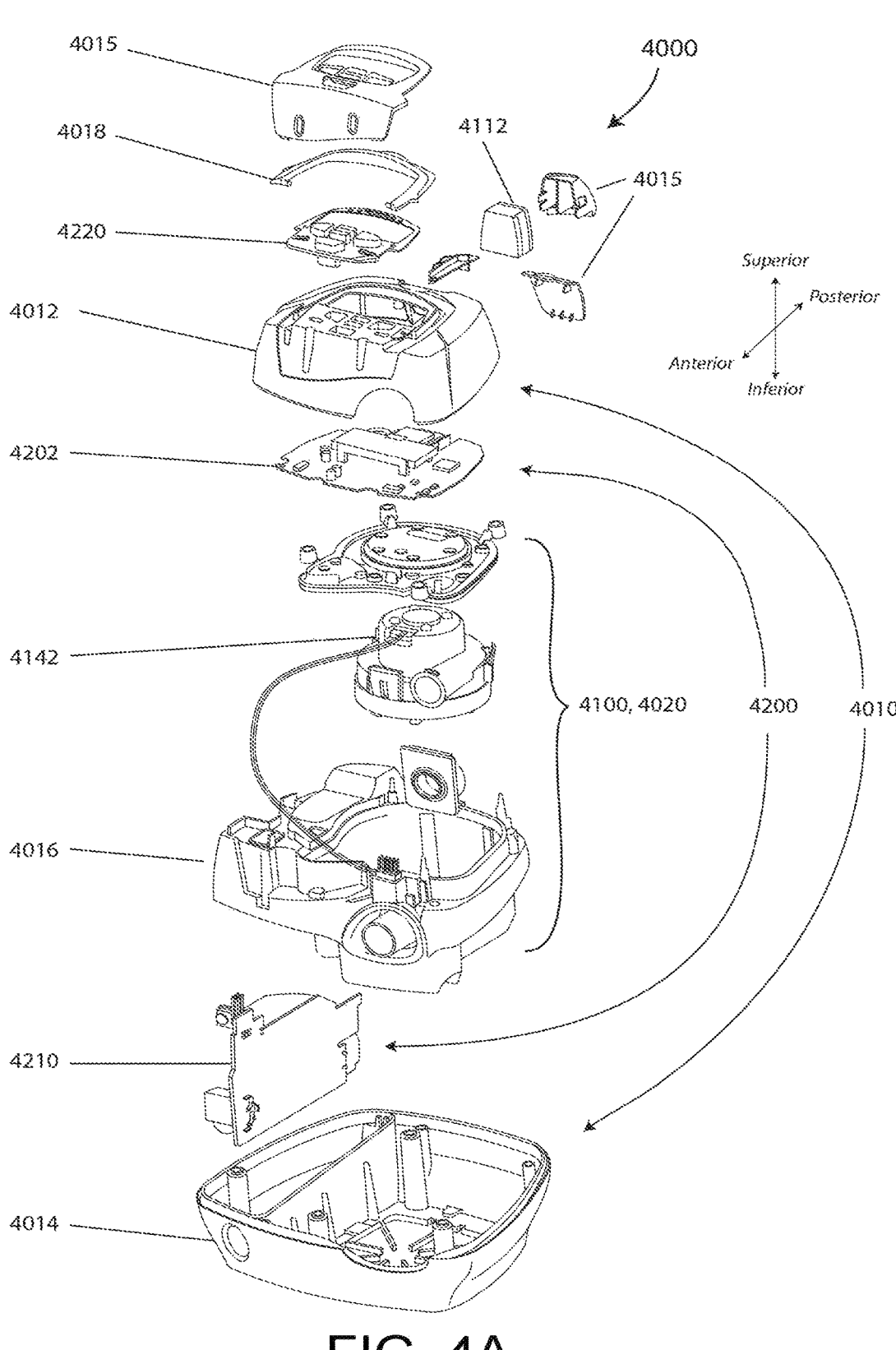
Figure 4B:
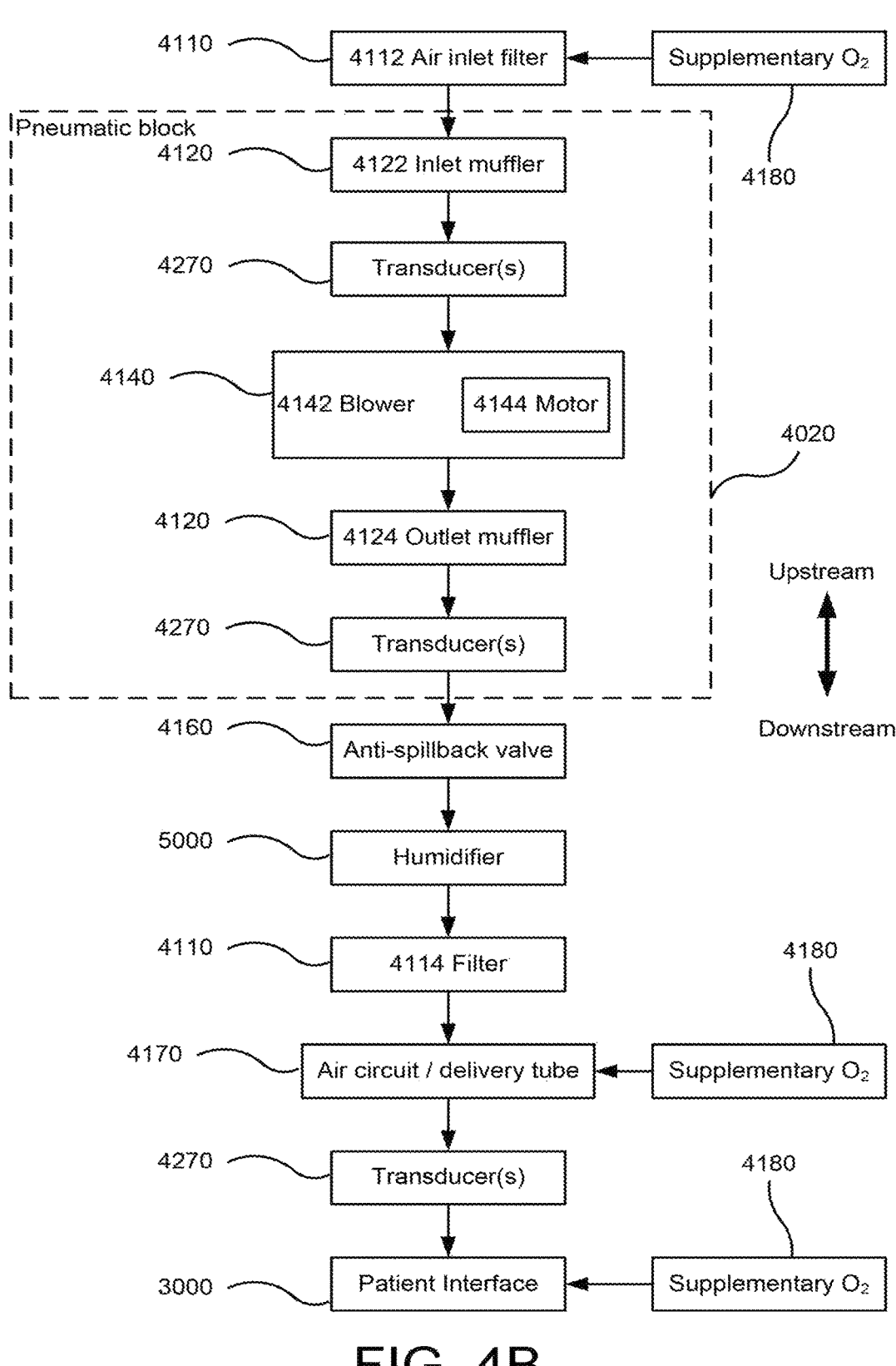
Figure 5A:
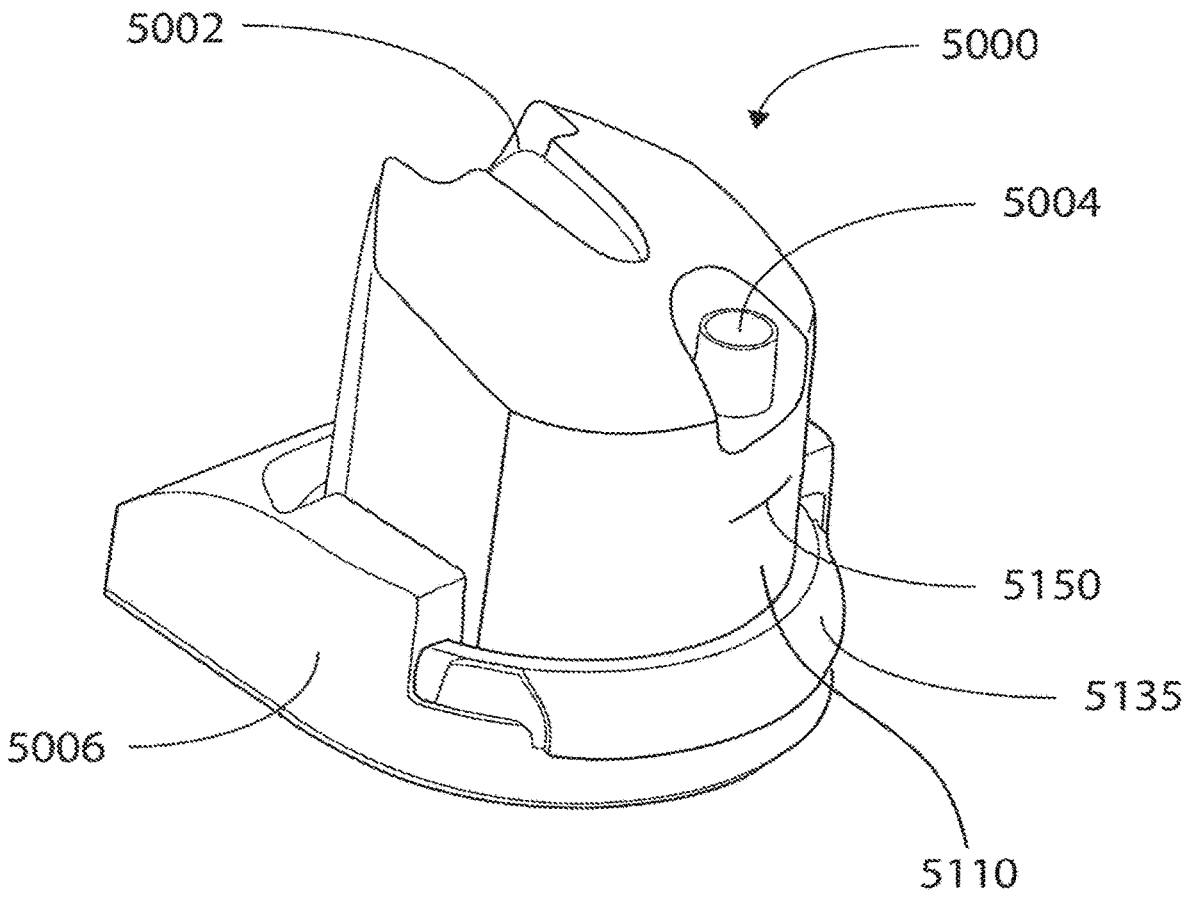
FIG. 5A shows an isometric view of a humidifier in accordance with one form of the present technology.

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

Figure 5B:
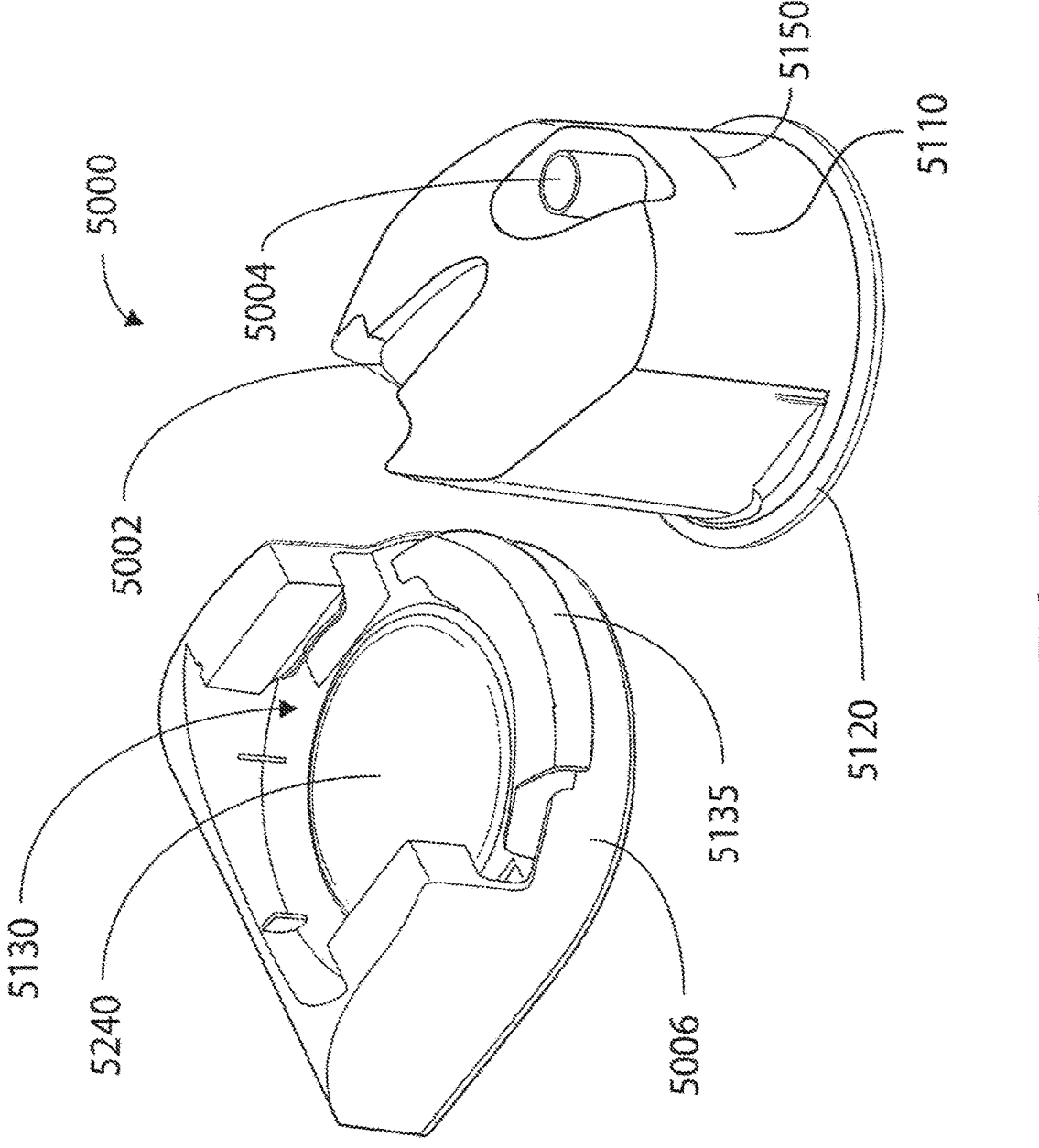
FIG. 5B shows an isometric view of a humidifier in accordance with one form of the present technology, showing a humidifier reservoir 5110 removed from the humidifier reservoir dock 5130.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

4.6 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak-0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

4.6.1 Wound Screening, Diagnosis, and Monitoring

Hospital admissions due to wounds and associated complications are becoming more expensive and frequent, in part due to the prevalence of diabetes and foot ulcers. Early prevention strategies and wound management are essential to identify infected wounds early, or properly manage chronic wounds and ulcers that have difficulty healing. Furthermore, screening of wounds at early stages may prevent hospital admission for wounds that can be managed by the patient or through telemedicine.

Accordingly, systems and methods have been developed to monitor, diagnose, and predict the course of a wound to aid in determining whether a wound is properly healing. This includes systems and methods that may be performed by the patient in the home in some cases, and some that utilized sensors available on mobile devices. Thus, patients may be able to manage wounds at home without the intervention of caregivers and reduce the costs of admission to hospitals. Furthermore, the systems and methods may determine when an infection is likely developing to immediately alert the patient and caregivers, so that infected wounds do not advance to a point of severity that requires costly intervention.

For instance, with daily or other regularly monitoring at home of the visual and heat profile of wounds, the system and methods disclosed herein may be able to detect signs of infection much earlier than when a patient would normally seek care for their wound. Additionally, with patients that are unsure of whether their wound is likely infected or otherwise needs intervention by a caregiver, the disclosed systems and methods allow the patient to have confidence that the wound can be properly managed at home or with minimal oversight from a provider.

4.7 Wound Monitoring Systems

FIG. 7 illustrates an example of a wound monitoring system according to the present disclosure. The system may include a patient 1000 with a wound 8000 and a mobile device 7300 with a camera 8005. The wound 8000 may be any kind of wound, including a wound to the skin or other wound that may be visible with a camera 8005 or other external sensor such as an infrared sensor 8010. The wound 8000 may be a trauma wound, surgical incision, a diabetic ulcer, pressure ulcer, or other visible wounds. The wound 8000 may be different sizes, and may be at any stage of the healing process. The wound 8000 could also be a bruise that did not penetrate the surface of the patient's 1000 skin.

The camera 8005 may be a camera incorporated into a mobile device 7300 or may be an external and separate camera 8005. In some examples, the camera 8005 may be utilized to capture images of the wound 8000. The camera may be a color or black and white camera, and may include multiple cameras to detect images from different points of view.

The infrared sensor 8010 may be any suitable sensor or detector that can detect infrared wavelengths emitted from the wound 8000. Accordingly, the output from the infrared sensor 8010 may be utilized to determine temperature features of the wound 8000. In other examples, other available heat sensors known in the art may be utilized.

In some examples additional sensors may be included for performing LIDAR based scanning of a wound. For instance, the system may include a laser light illuminator and light sensor for sensing the reflected laser light in order to construct a three dimensional model of a wound.

The mobile device 7300 may be a cell phone, tablet, or other suitable computing device. The mobile device 7300 may be connected to a wired or wireless network 7090 and may transmit image data and other data related to the wound 8000 over the network 7090. The mobile device 7300 may include a display and interactive user interface (e.g. touch screen).

The network 7090 may be connected to other computing device 8020 and displays 8015, and may also be connected to a server 7100 and database 7200. In some examples, the processing of image data and other sensor data may take place on the mobile device 7300, on the computing device 8020 or on the remote server 7100. In some examples, certain portions of the processing (e.g. computer vision) that require heavier CPU load may take place on the server 7100. In some examples, scaled down versions of machine learning algorithms may run locally on the mobile device 7300.

4.8 Wound Monitoring Methods

FIG. 8 is a flow chart illustrating an example process for monitoring, diagnosing and predicting a wound trajectory. In some examples, these steps are performed by a mobile device 7300, computing device 7020, or on a remote server 7100. Various steps may be performed on separate computing devices and control systems or the steps may all be performed by a single processor.

In one example, a patient 1000 or caregiver may capture an image of the wound 8000 and the image may be received by a processor 9000. This may include a color image 9105 and/or infrared data output by an infrared sensor 8010.

Next, the system may process the image to identify wound boundaries 9010. This may include determining the locations of pixels that represent a perimeter of the wound 8000. For instance, a color change threshold from typical wound colors, hues or textures, to a native hue of a patient's 1000 skin may indicate the wound boundaries. In some examples, changes in height or depth detected by LIDAR or similar sensors may be utilized to detect the wound boundaries. Additionally, various computer vision processing techniques are available to identify a wound and its boundaries as known to those of skill in the art. In other examples, identifying the wound boundaries 9010 may include mapping the entire surface area of the wound 8000. Additionally, infrared measurements may be mapped to the wound boundaries to determine which measurements output from the infrared sensor are within the wound boundaries.

Next, the system may identify wound features within the wound boundaries 9020. This may include temperature 9215 (output from the infrared sensor), size of the wound 9220, and color of the wound 9225. The temperature data 9215 may include a variety of features, including:

average temperature;

maximum temperature;

temperature difference between wound/non-wound;

maximum temperature difference; and others.

The temperature features 9215 may be determined based on the output of the infrared sensor or other temperature sensor and may be determined in combination with the wound boundary information from the color images.

The system may also identify the size of the wound 9220 based on the image data including by using algorithms that identify the perimeter of the wound or other methods. For instance, Ozturk C., et al, discloses basic methods in its 1995 paper "Measurement of wound healing by image analysis," which is incorporated herein by reference in its entirety. Additionally, and more recently, Yang et al., disclosed various methods in its 2016 paper "Sequential Change of Wound Calculated by Image Analysis Using a Color Patch Method during a Secondary Intention Healing," the content of which is incorporated herein by reference in its entirety. The system of the wound 9220 may include a variety of features, including:

surface area;

depth;

circumference; and others.

In some examples, a depth sensor such as LIDAR or other suitable sensors could be utilized to determine the depth of a wound. In some instances, a reference color and/or sized item may be required to be placed on the skin next to the wound 8000 to provide a color and size calibration. In other examples disclosed herein where multiple images are taken, the relative changes in color and/or size (rather than absolute sizes or colors) between images are utilized to make predictions.

The system may also identify the color 9225 or various other optical features of the images of the wound 8000. These features may primarily be determined from the image data output from the camera 8005. For instance, various colors 9225 may indicate or relate to various stages of wound healing, including white, red, and browning scabbing for instance. Additionally, various colors 9225 may indicate inflammation, or infection of a wound.

In some examples, various machine learning algorithms may be able to identify a type of wound and a wound stage from the image and/or infrared data. Generally, wounds that have impaired healing, including acute and chronic wounds, fail to progress properly through the normal stages of healing. For instance, many wounds enter a stage of pathologic inflammation due to defects in the healing process.

Wounds that heal normally typically progress through the following distinct phases, from: (1) hemostasis (blood clotting), (2) inflammation, (3) proliferation, and (4) maturation. Hemostasis involves coagulation and formation of a fibrin mesh that stablishes the platelet masses into a clot.

Inflammation is the stage that where neutrophils and other white blood cells enter the wound, destroy bacteria and remove debris. This stage peak around 24 to 48 hours after the wound was suffered. Additionally, macrophages enter the wound at this stage and secrete growth factors to start tissue repair. This stage lasts from four to six days and can be accompanied by edema (swelling), erythema (reddening of the skin), temperature increases, and pain. Accordingly, features to identify during this stage include red color and temperature elevation.

Proliferation is the stage where the tissue is repaired filled in, and the wound gap contracts. First, shiny, deep red granulation tissue fills the wound bed with connective tissue, and new blood vessels are formed. During contraction, the wound margins contract. Finally, epithelial cells cover the wound to form skin. This phase lasts from four to 24 days. Accordingly, the different tissue types (granulation tissue and epithelial cells) may be detected by an image process to confirm entry into the proliferation stage.

During the maturation, the tissue gains strength and flexibility, including by the organization of collagen fibers. This stage various considerably, and could last from 21 days to two years. Of course, this stage is likely the least important to the health of the patient, but could have considerable cosmetic implications. Accordingly, disclosed are systems and methods that maximize wound healing conditions for the best cosmetic outcomes.

Accordingly, the color 9225, temperature, and other features disclosed herein, may be utilized to detect the stage of wound healing and how the wound 8000 is progressing through a particular stage. In addition to color, the image recognition algorithms may identify the texture of scabbing, other textures, shapes, etc. to identify additional relevant wound features for determining a wound trajectory. Also, the system may input data other data from the patient 100 including date of wound, diet, sleep score output from various medical devices including sleep apnea machines, known conditions impacting healing like diabetes, and others. Thus, the system may utilize this additional information to determine the wound healing trajectory.

Accordingly, once the computer vision algorithms have identified the relevant wound 8000 features, the system may determine a healing trajectory 9030. The healing trajectory may include a variety of outputs, including the following:

wound healing stage;

time remaining to heal;

progress versus average based on the timeline;

quantitative measures of wound progress;

augmented reality showing predicted wound shrinking;

images that have been automatically adjusted to show wound progress changes, including by changing color, texture, and size of wound in captured images;

indications that wound is following behind on healing trajectory and intervention is required;

indication that wound is infected and intervention is required, including based on color, temperature, and subjective pain levels;

example images of a what a similar wound will look like in a week, two weeks, or three weeks, for instance; and others.

Then, the system may display the trajectory 9040 on the mobile device 7300 or other computing devices and display 8015. This may include images (or predicted modified images) of the wound 8000.

The system could also analyse the healing trajectory to determine if an alert is necessary 9050. For instance, the system may also send a notification or alert 9060 if the wound 8000 does not heal fast enough, it is likely infected, or is having other issues. The alert may issue from the mobile device 7300 or other computing device 8020. This may include determining a trajectory, and whether the trajectory is above a minimum acceptable threshold trajectory or healing time. Additionally, the system may analyse the images for signs of injection that may include:

expanding redness around the wound 8000;
  yellow or greenish-colored pus or cloudy wound drainage (in this example, the system may be trained to recognize pus);
  fever; and
  others.

Additionally, the system may generally send an alert if the wound is not healing or not improving or any of the detected wound features are getting worse. In some examples, a rising temperature above a threshold may indicate an infection or a sustained temperature within a certain range may indicate an infection or retarding of wound healing progress. Thus, the system could send a variety of notifications including:

an SMS message to the mobile device 7300;
  call the mobile device 7300;
  alert the care giver;
  issue an alert with the application; or
  others.

FIG. 9 illustrates another example of a monitoring process that includes processing images from more than one point in time during the healing process. For instance, the system may receive a first image of the wound 9000 with a first time stamp 10000 and receive a second image of the wound 9000 with a second time stamp 10000. Then, the system may determine the time elapsed between the two images. Accordingly, this can be utilized to determine or estimate the trajectory of the wound 9000 based on its improvement rate.

For instance, as disclosed herein, the wounds boundaries could be identified 9010 and then the wound features within those boundaries could be identified 9020. This could be performed for both images. In some examples, the system may first determine a likelihood the wound is the same wound, based on the time elapsed and the similarity of the features.

Next, when the wound healing trajectory is determined 9030 the system may determine a feature trend 10010 and/or determine a rate of change of the features 10020. For instance, the system could determine how fast the surface area of the wound 9000 is decreasing, including in relation to the wound 9000 on the healing timeline and/or stage. Additionally, color changes, or time in various stages could be utilized to determine a trend.

The trends 10010 could then be utilized to extrapolate a healing trajectory based on the trends 10010 and the starting date or point. Accordingly, the healing trajectory could then be displayed 9040 which may include a predicted image of a wound 10020 and/or a predicted timeline for recovery 10020. The predicted image of the wound in a week, for instance, could include an edited the image where the system shrinks the wound 8000 size and/or changes the color. In other examples, the system may include stock images to display to the patient 1000 predicting the course of the wound 8000.

In other examples, the system may utilize two, three, four, five images of a wound 9000 to determine a trend and trajectory 9030. In other examples, the user could be instructed to take a picture of the wound 8000 daily, every other day, or weekly to update the trajectory 9040.

4.9 Wound Monitoring and Sleep Monitoring

In some examples, the system may also input sleep quality metrics that are output by a respiratory therapy device 4000 to modify the predicted healing trajectory 9030. This may include sleep quality (e.g. sleep score) or may include total sleep time per night. In some examples, the system could train a model of healing based on user data from various images and sleep data, to determine how much an improvement in sleep will improve the healing time.

In other examples, the predicted time to healing could be automatically modified based on the patient's 1000 sleep score. Additionally, the system could determine a target amount of sleep for a patient 1000 to improve the healing timeline a threshold amount.

4.10 Glossary

For the purposes of the present technology disclosure, in certain forms of the present technology, one or more of the following definitions may apply. In other forms of the present technology, alternative definitions may apply.

4.10.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Patient: A person, whether or not they are suffering from a respiratory condition.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

4.10.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker.

Polycarbonate: a thermoplastic polymer of Bisphenol-A Carbonate.

4.11 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

SELECTED EMBODIMENTS

Although the above description and the attached claims disclose a number of embodiments of the present invention, other alternative aspects of the invention are disclosed in the following further embodiments.

1. A system for monitoring a wound, the system comprising:

a display a camera configured to output image data;

a memory containing machine readable medium comprising machine executable code having stored thereon instructions;

a control system coupled to the memory comprising one or more processors, the control system configured to execute the machine executable code to cause the control system to:

receive a first image output from the camera;

process the image to identify a portion of the pixels within the first image that represent a wound;

process the portion to identify a set of wound features;

determine healing trajectory based on the set of wound features; and display the healing trajectory on the display.

2. The system of embodiment 1, wherein the set of wound features comprise at least one: a temperature sensed using an infrared sensor, a wound size, or a color.

3. The system of embodiment 2, wherein the wound size comprises wound diameter, wound surface area, or wound depth.

4. The system of any one of embodiments 1-3, wherein the healing trajectory comprises a healing time, a predicted decrease in wound size within a time window, or a color change.

5. The system of embodiment 4, wherein the control system is further configured to process the first image to output a predicted image of the wound after a first time interval.

6. The system of embodiment 5, wherein processing the first image comprises altering the color of a subset of the portion of the pixels.

7. The system of any one of embodiments 5-6, wherein determining the healing trajectory further comprises receiving a first input from a user interface.

8. The system of embodiment 7, wherein the first input comprises a time of receiving the wound and wherein determining the healing trajectory further comprises comparing the time of receiving the wound to a time stamp on the first image.

9. The system of any one of embodiments 1-8, wherein the healing trajectory comprises determining whether the wound is closest to a first or second milestone of a typical wound healing trajectory.

10. The system of embodiment 9, wherein the control system is further configured to display a stock image associated with the determined first or second milestone.

11. A method for monitoring a wound, the method comprising:

receiving a first image output from a camera with a first time stamp and a second image output from the camera with a second time stamp;

comparing the first and second time stamps to determine a time period between the first and second images;

processing the first and second images to identify a first portion of the first image and a second portion of the second image that represent a wound;

comparing the wound identified in the first and second images to confirm it is the same wound;

processing the first portion to identify a first set of wound features and processing the second portion to identify a second set of wound features;

processing the first and second set of wound features and the time period to determine a healing trajectory; and displaying the healing trajectory on the display.

12. The method of embodiment 11, wherein processing the first and second set of wound features comprises determining a trend of at least one of the first and second set of wound features.

13. The method of embodiment 12, wherein the trend comprises a linear, a logarithmic, or a parametric trajectory.

14. The method of any one of embodiments 11-13, wherein processing the first and second set of wound features comprises determining a rate of change of at least one of the first and second set of wound features.

15. The method of any one of embodiments 11-13, wherein determining the healing trajectory further comprises receiving a first input from a user interface.

16. The method of embodiment 15, wherein the first input comprises at least one of: existing patient health conditions that impact wound healing, activity level, diet, medication, or pain level.

17. The method of any one of embodiments 12-16, wherein the trend comprises a rate of change and is compared to an expected rate of change to determine whether the wound is healing significantly faster, slower than normal, or worsening.

18. The method of embodiment 17, further comprising send an alert notification if it is determined that the wound is healing significantly slower than normal or worsening.

19. The method of any one of embodiments 11-18, wherein processing the first and second set of wound features comprises inputting the first and second set of wound features into a machine learning algorithm trained with images of wounds of the same type.

20. The method of any one of embodiments 11-19, wherein the first and second set of wound features comprises infrared depth measurements.

21. The method of embodiment 20, wherein processing the first and second set of wound feature comprises determining a change in average depth of the wound.

22. A computer program product comprising instructions which, when executed by a control system, cause the computer to carry out the method of any one of embodiments 11 to 21.

23. The computer program product of embodiment 22, wherein the computer program product is a non-transitory computer readable medium.

24. A control system comprising:

one or more processors;

a memory having stored thereon machine readable instructions;

wherein the one or more processors are coupled to the memory, and the method of any one of embodiments 11 to 21 is implemented when the machine readable instructions in the memory are execute by at least one of the one or more processors of the control system.

The invention claimed is:

1. A system for monitoring a wound, the system comprising:

a display;

a camera configured to output image data;

a memory containing machine readable medium comprising machine executable code having stored thereon instructions; and a control system coupled to the memory comprising one or more processors, the control system configured to execute the machine executable code to cause the control system to:

receive a first image output from the camera;

process the first image to identify a portion of pixels within the first image that represents the wound;

process the portion to identify a set of wound features;

evaluate, with a machine learning algorithm, the set of wound features to (i) identify a type of wound, (ii) identify a wound stage for the wound, or (ii) both the above (i) and (ii); and present, via the display, an indication of (i) the type of wound, (ii) the wound stage for the wound, or (iii) both the above (i) and (ii);

generate, based on the first image, a predicted image of the wound after a first time interval, wherein the predicted image is an edited version of the first image.

2. The system of claim 1, wherein the control system is further configured to:

determine, based on (i) the type of wound, (ii) the wound stage for the wound, or (iii) both the above (i) and (ii), that the wound is healing unsatisfactorily;

generate, based on the determination that the wound is healing unsatisfactorily, an alert; and transmitting, automatically, to a user, the alert.

3. The system of claim 2, wherein the determination that the wound is healing unsatisfactorily is based on (i) an expanding redness around the wound, (ii) pus or wound drainage, (iii) temperature, or any combination of the above (i)-(iii).

4. The system of claim 1, wherein the set of wound features comprise at least one of: a temperature sensed using an infrared sensor, a wound size, and a color.

5. The system of claim 4, wherein the wound size comprises at least one of: wound diameter, wound surface area, and wound depth.

6. The system of claim 1, wherein the predicted image depicts the wound as (i) a different size, (ii) a different color, (iii) or both the above (i) and (ii).

7. The system of claim 6, wherein processing the first image comprises altering the color of a subset of the portion of the pixels.

8. A system for monitoring a wound, the system comprising:

a display;

a camera configured to output image data;

a memory containing machine readable medium comprising machine executable code having stored thereon instructions; and a control system coupled to the memory comprising one or more processors, the control system configured to execute the machine executable code to cause the control system to:

receive a first image output from the camera;

process the first image to identify a portion of pixels within the first image that represents the wound;

process the portion to identify a set of wound features;

determine, based on the set of wound features, that the wound is healing unsatisfactorily;

generate, based on the first image, a predicted image of the wound after a first time interval, wherein the predicted image is an edited version of the first image;

generate, based on the determination that the wound is healing unsatisfactorily, an alert; and transmit, automatically to a user, the alert.

9. The system of claim 8, wherein the control system is further configured to:

evaluate, with a machine learning algorithm, the set of wound features to (i) identify a type of wound, (ii) identify a wound stage for the wound, or (ii) both the above (i) and (ii); and present, via the display, an indication of (i) the type of wound, (ii) the wound stage for the wound, or (iii) both the above (i) and (ii).

10. The system of claim 8, wherein the alert is one or more of a text message sent to a mobile device, a phone call to the mobile device, an alert presented to a caregiver, and an alert issued within an application.

11. The system of claim 8, wherein the determination that the wound is healing unsatisfactorily is based on (i) an expanding redness around the wound, (ii) pus or wound drainage, (iii) temperature, or any combination of the above (i)-(iii).

12. The system of claim 8, wherein the set of wound features comprise at least one of: a temperature sensed using an infrared sensor, a wound size, and a color.

13. The system of claim 12, wherein the wound size comprises at least one of: wound diameter, wound surface area, and wound depth.

14. The system of claim 8, wherein the predicted image depicts the wound as (i) a different size, (ii) a different color, (iii) or both the above (i) and (ii).

15. The system of claim 14, wherein processing the first image comprises altering the color of a subset of the portion of the pixels.

16. A method for monitoring a wound, the method comprising:

receiving, from a camera configured to output image data, a first image;

processing, via a control system, the first image to identify a portion of pixels within the first image that represents the wound;

processing, via the control system, the portion to identify a set of wound features;

evaluating, with a machine learning algorithm, the set of wound features to (i) identify a type of wound, (ii) identify a wound stage for the wound, or (ii) both the above (i) and (ii);

presenting, via a display, an indication of (i) the type of wound, (ii) the wound stage for the wound, or (iii) both the above (i) and (ii);

determining, based on the set of wound features, that the wound is healing unsatisfactorily;

generating, based on the first image, a predicted image of the wound after a first time interval, wherein the predicted image is an edited version of the first image;

generating, based on the determination that the wound is healing unsatisfactorily, an alert; and transmitting, automatically to a user, the alert.

17. The method of claim 16, wherein the alert is one or more of a text message sent to a mobile device, a phone call to the mobile device, an alert presented to a caregiver, and an alert issued within an application.

18. The method of claim 16, wherein the determination that the wound is healing unsatisfactorily is based on (i) an expanding redness around the wound, (ii) pus or wound drainage, (iii) temperature, or any combination of the above (i)-(iii).

19. The method of claim 16, wherein the set of wound features comprise at least one of: a temperature sensed using an infrared sensor, a wound size, and a color.

20. The method of claim 16 wherein the predicted image depicts the wound as (i) a different size, (ii) a different color, (iii) or both the above (i) and (ii).

* * * * *